United States Patent [19]

Krüger et al.

[11] Patent Number: 4,491,466

[45] Date of Patent: Jan. 1, 1985

[54] 1,2,3-THIADIAZOLE-5-YL-UREA DERIVATIVES, PROCESSES FOR THEIR USE AS PLANT GROWTH REGULATING AND DEFOLIATING AGENTS

[75] Inventors: Hans-Rudolf Krüger; Friedrich Arndt; Reinhard Rusch, all of Berlin, Fed. Rep. of Germany

[73] Assignee: Schering AG, Berlin and Bergkamen, Fed. Rep. of Germany

[21] Appl. No.: 424,987

[22] Filed: Sep. 27, 1982

[30] Foreign Application Priority Data

Oct. 1, 1981 [DE] Fed. Rep. of Germany ....... 3139506

[51] Int. Cl.³ .................... C07D 285/06; A01N 43/82
[52] U.S. Cl. .......................................... 71/90; 548/127
[58] Field of Search ............................. 548/127; 71/90

[56] References Cited

U.S. PATENT DOCUMENTS

| | | | |
|---|---|---|---|
| 3,883,547 | 5/1975 | Schulz et al. | 548/127 |
| 4,181,517 | 1/1980 | Krüger et al. | 548/127 |
| 4,259,502 | 3/1981 | Krüger | 548/127 |
| 4,358,596 | 11/1982 | Krüger | 548/127 |

FOREIGN PATENT DOCUMENTS

| | | | |
|---|---|---|---|
| 2031889A | 4/1980 | United Kingdom | 548/127 |
| 2039889A | 8/1980 | United Kingdom | 548/127 |

*Primary Examiner*—Robert Gerstl
*Attorney, Agent, or Firm*—Michael J. Striker

[57] ABSTRACT

New 1,2,3-thiadiazole-5-yl-urea derivatives of the formula

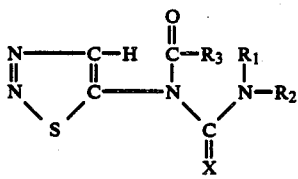

wherein $R_1$ is hydrogen or a $C_1$-$C_4$ alkyl group which may be interrupted by one or more sulfur or oxygen atoms, $R_2$ is a $C_1$-$C_4$ alkyl which may be interrupted by one or more sulfur or oxygen atoms, a cycloaliphatic hydrocarbon group which may be substituted by one or more alkyl groups, an aromatic hydrocarbon group which may be substituted by one or more members of the group consisting of alkyl, halogen, alkyl thio, alkoxy, trifluoromethyl and nitro, or a heterocyclic hydrocarbon group which may be substituted containing at least one nitrogen atom, $R_3$ is hydrogen, a $C_1$-$C_{10}$ alkyl group which may be substituted, a $C_2$-$C_8$ alkenyl, an aryl-$C_1$-$C_2$ alkyl, a $C_3$-$C_8$-cycloaliphatic hydrocarbon group which may be substituted with one or more $C_1$-$C_6$ alkyl groups, and an aromatic hydrocarbon group which may be substituted with one or more members of the group consisting of $C_1$-$C_6$ alkyl, halogen, $C_1$-$C_6$-alkoxy and trifluoromethyl, and X is oxygen or sulfur. Processes for making these compounds, compositions containing these compounds having plant growth regulating and defoliating activity and methods for using these compounds for these purposes are also disclosed and claimed in the application.

14 Claims, No Drawings

1,2,3-THIADIAZOLE-5-YL-UREA DERIVATIVES, PROCESSES FOR THEIR USE AS PLANT GROWTH REGULATING AND DEFOLIATING AGENTS

BACKGROUND OF THE INVENTION

This invention relates to new 1,2,3-thiadiazole-5-yl urea derivatives, processes for making these compounds, plant growth and defoliating agents containing these compounds as active substances and processes for using these compounds to achieve plant growth and defoliating action.

1,2,3-thiadiazole-5-yl-urea derivatives possessed of plant growth and defoliating activity are already known (DE-OS No. 2,214,632; DE-OS No. 2,506,960). Thus 1-phenyl-3-(1,2,3-thiadiazole-5-yl)-ureas are known as cotton plant defoliants. It is, however, desired to provide more effective defoliants and/or plant growth regulators than these known compounds.

It is, therefore, an essential object of this invention to provide new, 1,2,3-thiadiazole-5-yl-urea derivatives which are structural analogs of the known cotton defoliants but which are more effective in their defoliating activity than the known compounds and that even when used in smaller quantities.

According to the invention, this and other objects and advantages are achieved through the provision of 1,2,3-thiadiazole-5-yl-urea derivatives of the formula

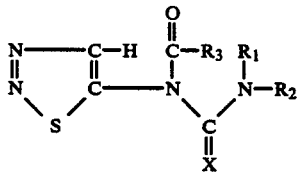

wherein $R_1$ is hydrogen or a $C_1$-$C_4$ alkyl group which may be interrupted by one or more sulfur or oxygen atoms, $R_2$ is a $C_1$-$C_4$ alkyl group which may be interrupted by one or more sulfur or oxygen atoms, a cycloaliphatic hydrocarbon group which may be substituted by one or more alkyl groups, an aromatic hydrocarbon group which may be substituted by one or more members of the group consisting of alkyl, halogen, alkylthio, alkoxy, trifluoromethyl and nitro or a heterocyclic hydrocarbon group which may be substituted containing at least one nitrogen atom, $R_3$ is hydrogen, a $C_1$-$C_{10}$ alkyl group which may be substituted, a $C_2$-$C_8$ alkenyl, an aryl-$C_1$-$C_2$-alkyl, a $C_3$-$C_8$-cycloaliphatic hydrocarbon group which may be substituted with one or more $C_1$-$C_6$ alkyl groups, or an aromatic hydrocarbon group which may be substituted for one or more members of the group consisting of $C_1$-$C_6$-alkyl, halogen, $C_1$-$C_6$-alkoxy and trifluoromethyl and X is oxygen or sulfur.

The compounds of the invention are excellently suitable for defoliating cotton plants and this regard markedly surpass the known agents of analogous structure and activity. The use of mechanical cotton pickers for picking the cotton balls is thereby made possible.

On normal cotton plants which are not treated with defoliating agents, the bolls on the lower branches open first while the bolls on the upper branches continue to open slowly over a period of as long as two months from the time when picking of the lower bolls is desirable. The majority of the leaves remain attached to the plant and cause green stains on the cotton when mechanical cotton pickers are employed. In addition, the leaves high on the plant shade the lower bolls from sunlight an air resulting in excessive boll rot. At times, 15% of the cutton crop has been lost because of this boll rot. Without the use of defoliating agents, numerous hand pickings are necessary to prevent boll rot and staining.

It is the discovery of this invention that the foliage of cotton plants may be treated with many types of the herein described 1,2,3-thiadiazole-5-yl-urea derivatives with the result that the leaves are shed.

The compounds of the invention are also excellently suitable for regulating plant growth by retarding the vegetative growth thereof. Observation of the operation of the defoliant ingredient indicates that when properly applied a true hormonetype action is involved, and the defoliant operates by a true translocation within the plant system. The regulation of the plant growth which is achieved by application of the compounds of the invention is visually recognized and can be appreciated by a change in the plant size, particularly in its height, its shape or color or by the change in structure of the treated plant or of its parts, i.e., roots, stems, buds, leaves, etc.

For example, the following changes in the plant may be observed in addition to the defoliation:
Inhibition of vertical growth.
Inhibition of root development.
Stimulation of bud development.
Intensification of the plant coloration, etc.

The compounds of the invention may be used either alone or in a mixture with one another or with other active substances. Optionally, other plant protection or pest control agents, such as fungicides, nematocides, or other agents may be added, according to the desired purpose. The addition of fertilizers may also be desirable or preferable.

Depending on the purpose of use, other substances may also be added, for example non-phytotoxic components which can produce with herbicides a synergistic increase of action, such as wetting agents, emulsifiers, solvents, oily additions and the like.

The quantities used for the desired regulation of plant growth are, as a rule 0.05 to 5 kg active substance per hectare.

The manner of the growth regulating effect, however, depends on the treatment time and, not least on the type of plant involved. Against certain weeds in the early stage or the start of sprouting, the inhibition may occur in a manner which equals, for example total inhibition of development of a wasteland flora including shrubbery. The chemical compounds of the invention can be used also where it is desired not to fully destroy flora at once, but to maintain it in a vegetative low growth stage.

Appropriately, the active substances according to the invention or their mixtures are used in the form of suitable preparations, such as powders, scatters, granulates, solutions, emulsions or suspensions, with the addition of a liquid and/or solid vehicle or diluent and also of a wetting, adhesive emulsifying and/or dispersing agent.

Suitable liquid vehicles are water, aliphatic and aromatic hydrocarbons, such as benzene, toluene, xylene, cyclohexanone, isophorone, dimethylformamide, and mineral oil fractions.

As solid vehicles, there come into consideration the mineral earths, such as siliceous clay, silica gel, talc, kaolin, attaclay, limestone, silicic acid and plant products, such as flours.

Among surface active substances there may be mentioned calcium-lignin sulfonate, polyoxyethyleneoctylphenolether, naphthelene-sulfonic acids and their salts, phenosulfonic acids and their salts, formaldehyde condensates, fatty alcohol sulfates and substituted benzene sulfonic acids and their salts.

The proportion of the active substance or substances in the various preparations may vary within wide limits. The agents contain for example about 5% to 95% by weight of active substances, about 95% to 5% by weight of liquid or solid vehicles as well as possibly up to 20% by weight of surface active substances.

The application of the agents may be effected in the usual manner, such as with water as vehicle in total spray quantities of 100 to 5000 liters/ha. An application of the agents in the so-called "ultra-low-volume process" is likewise possible, as is their application in the form of so-called microgranulates.

The type and manner of achieving the desired plant growth regulation is of course dependent on the treatment time, i.e. at what time in the plant life cycle it is carried out, the type of plant, the concentration of the active agent, etc. but this is all part of the art.

Compounds of the invention, which have been found to be particularly effective are those in which in formula I $R_1$ is hydrogen, $C_1$-$C_4$-alkyl as for example methyl, ethyl, isopropyl, propyl or butyl, $R_2$ is $C_1$-$C_4$-alkyl as for example methyl or ethyl, $C_5$-$C_8$cyclo-alkyl as for example cyclopentyl, cyclohexyl or methylcyclohexyl, aryl as for example phenyl, halogenophenyl, $C_1$-$C_4$-alkylphenyl, $C_1$-$C_4$-alkoxyphenyl, nitrophenyl or trifluoromethylphenyl, $R_3$ is hydrogen, $C_1$-$C_{10}$-alkyl as for example methyl, ethyl, propyl, n-butyl, 1-ethylpropyl, tert.-butyl, n-heptyl, n-nonyl or n-decyl, fluoromethyl, methoxymethyl, phenoxymethyl, 1-phenoxyethyl, 2-phenoxyethyl, or (2,4-dichlorophenoxy)-methyl, $C_2$-$C_8$-alkenyl as for example 2-butenyl, 2-methyl-2-propenyl or propene-1-yl, aryl-$C_1$-$C_2$-alkyl as for example benzyl, 4-chlorobenzyl, $C_3$-$C_8$-cycloalkyl as for example cyclopropyl, cyclopentyl, cyclohexyl or methylcyclohexyl, phenyl, 2-chlorophenyl, 3-chlorophenyl, 4-chlorophenyl, aryl as for example 2,4-dichlorophenyl, 2-methylphenyl, 3-methylphenyl, 4-methylphenyl, 3-nitrophenyl, 4-nitrophenyl, 2-methoxyphenyl, 4-methoxyphenyl, 1-naphthyl, 2-naphthyl or 2-furyl and X is oxygen or sulfur.

The compounds of the invention may be used alone or in the form of mixtures thereof or in admixture with other active substances. They can be advantageously combined with other defoliants, other plant protecting or noxious agents, depending on what effects are sought to be realized. Thus for example the compounds of the invention may be combined with herbicides when it is desired to achieve an inhibition of development of certain weeds, plants, shrubs and the like. Examples of such other active substances include the following: triazine, aminotriazole, anilide, diazine, uracil, aliphatic carboxylic acids and halogeno carboxylic acids, substituted benzoic acids and aryloxycarboxylic acids, hydrazide, amide, nitrile, esters of such carboxylic acids, carbamidic acid and thiocarbamidic acid, esters, 2,3,6-trichlorobenzyloxypropanil, rhodan containing agents and other like compounds.

There may also be included in the agents of the invention other non-phytotoxic aditives which for example with the herbicides provide a synergistic growth regulating effect. Such non-phytotoxic additives include emulsifying agents, dispersing agents, solvents and oil-type additives.

The compositions of the invention can include in their formulation other growth regulating and defoliating agents as for example
Auxin
α-(2-chlorophenoxy)-propionic acid
4-chlorophenoxyacetic acid
2,4-dichlorophenoxyacetic acid
indolyl-3-acetic acid
indolyl-3-butyric acid
α-naphthylacetic acid
β-naphthoxyacetic acid
naphthylacetamide
n-m-tolylphthalylamidic acid
gibberelline
S,S,S-tri-n-butyl-trithiophosphoric acid ester
cytokinine
2-chloroethylphosphonic acid
2-chloro-9-hydroxyfluorene-9-carboxylic acid
2-chloroethyl-trimethylammoniumchloride
N,N-dimethylaminosuccinic acid amide
2-isopropyl-4-trimethylammonio-5-methylphenyl-piperidine-1-carboxylic acid ester chloride
phenyl-isopropylcarbamate
3-chlorophenyl-isopropylcarbamate
ethyl-2-(3-chlorophenylcarbamoyloxy)-propionate
maleic acid hydrazide
2,3-dichloroisobutyric acid
di-(methoxythiocarbonyl)-disulfide
1,1'-dimethyl-4,4'-bipyridylium-dichloride
3,6-endoxohexahydrophthalic acid,
3-amino-1,2,4-triazole
1,2,3-thiadiazolyl-5-yl-urea derivatives
1-(2-pyridyl)-3-(1,2,3-thiadiazole-5-yl)-urea
2-butylthio-benzthiazole
2-(2(methylpropylthio))-benzthiazole
3,4-dichloroisothiazole-5-carboxylic acid
2,3-dihydro-5,6-dimethyl-1,4-dithiin-1,1,4,4-tetraoxide
arsenic acid
cacodylic acid
chlorate, preferably calciumchlorate, potassiumchlorate
magnesium chlorate or sodium chlorate
calciumcyanamide,
potassium iodide
magnesiumchloride
abietic acid
nonanol As above noted the compounds in the form of their compositions can be used in the form of powders, scatters, granulates, solutions, emulsions or suspensions, with the addition of liquid and/or solid vehicles or diluents as well as wetting, adhesive, emulsifying and/or dispersing agents.

The compositions of the invention can for example be formulated as follows:

A. Spray Powder (a)

80 weight % active agent
15 weight % kaolin
5 weight % surface active agent on the basis of sodium salts of N-methyl-N-oleyl-taurine and the calcium salt of ligninsulfonic acid.

(b)

50 weight % active agent
40 weight % mineral clay
5 weight % cellulose pitch
5 weight % surface active agent on the basis of a mixture of calcium salt of ligninsulfonic acid with alkylphenylpolyglycol ethers.

(c)

20 weight % active agent
70 weight % mineral clay
5 weight % cellulose pitch
5 weight % surface active agent on the basis of a mixture of a calcium salt of ligninsulfonic acid with alkylphenylpolyglycol ethers.

(d)

5 weight % active agent
80 weight % tonsil
20 weight % cellulose pitch
5 weight % surface active agent on the basis of a fatty acid condensation product.

B. Emulsion Concentrate 20 weight % active agent
40 weight % xylene
35 weight % dimethylsulfoxide
5 weight % of a mixture of nonylphenylpolyoxyethylene or calciumdodecylbenzenesulfonate.

The compounds of the invention can be prepared by reacting a compound of the formula II $$\begin{array}{c} N \text{——} C\text{—}H \\ \| \quad \| \quad O \\ N \quad C\text{—}N\text{—}C\text{—}R_3 \\ \diagdown S \diagup \quad | \\ \quad \quad Z \end{array} \quad \text{II}$$

(a) with a compound of the formula $$\begin{array}{c} R_1 \\ \diagdown \\ N\text{—}CX\text{—}Cl \\ \diagup \\ R_2 \end{array} \quad \text{III}$$

preferably in the presence of an acid acceptor, or (b) if $R_1$ is hydrogen reacting said compound II with a compound of the formula $$R_2\text{—}N\text{=}C\text{=}X \quad \text{IV}$$

preferably in the presence of a catalyst, suitably an organic base for instance triethylamine wherein $R_1$, $R_2$, $R_3$ and X have the above-designated means and Z is hydrogen or an equivalent of an alkali or alkaline earth metal preferably sodium, potassium or lithium.

If Z is hydrogen, then the reaction is carried out in the presence of a base as for instance an alkali metal hydroxide, -alcoholate, -hydride or -caronate and most preferably a sodium compound.

A preferred method for effecting the reaction is with a compound of formula II wherein Z is hydrogen and wherein said compound is reacted with the compound of formula III or IV in the presence of a base as for example sodium hydride.

The reaction takes place at a temperature of between about 0° and 120° C. and in general at a temperature between about room temperature and the reflux temperature of the reaction mixture.

The time required for the reaction to complete itself amounts to from 1 to 72 hours.

The compounds of formula II are in part known or can be made by the known methods.

For carrying out the process for preparing the compounds of the invention, the reactants are used in equimolar amounts. Suitable reaction media are solvents inert with respect to the reactants. The choice of solvent or suspension agent depends on the correspondingly charged carbamoyl, thiocarbamoylchloride, isocyanate or isothiocyanate used, the acid accepter, and methyl compound which are selected for use in the reaction.

As solvent or suspension agent there comes into consideration the following: ethers such as diethylether, diisopropylether, tetrahydrofuran and dioxan, aliphatic and aromatic hydrocarbons such as petroleum ether, cyclohexane, hexane, heptane, benzene, toluene, and xylene, carboxylic acid nitriles such as a acetonitrile and carboxylic acid amides such as dimethylformamide.

As acid accepters there are suitable for use herein organic bases such as triethylamine, N,N-dimethylanilin and pyridine bases or inorganic bases such as oxides, hydroxides and carbonates of alkali metal and alkaline earth metals. Liquid bases such as pyridine can serve simultaneously as solvent for the reaction.

The compounds of the invention prepared as above described can be recovered from the reaction mixtures containing them by for example distilling off the solvent at normal or reduced pressure or through precipitation with water, whereby as a rule their alkali sensitivity can be favored by treatment in a weak acid milieu.

The compounds of the invention are as a rule colorless, odorless crystaline materials, difficultly soluble in water and aliphatic hydrocarbons but readily soluble in halogenated hydrocarbons such as chloroform and carbontetchloroform, ketones such as acetone, carboxylic acid amides such as dimethylformamide, sulfoxides such as dimethylsulfoxide, carboxylic acid nitriles such as a acetonitrile and lower alcohols such as methanol and ethanol. As solvents for crystallizing out the compounds of the invention there come into consideration tetrachlorinated hydrocarbons, chloroform, acetonitrile and toluene.

The following examples are given for illustrating the invention and are not to be construed as limiting the scope thereof in any way.

EXAMPLE I 1-acetyl-3-phenyl-1-(1,2,3-thiadiazole-5-yl)-urea 22.8 g (0.159 mol) acetic acid-N-(1,2,3-thiadiazole-5-yl)-amide were dissolved in 120 ml water free dimethylformamide and then reacted with 6.94 g (0.159 mol) of a 50% dispersion of sodium hydride in oil. During the addition, the mixture is through cooling maintained at 30° C. and thereafter is stirred for 30 minutes at room temperature until no further hydrogen is evolved. Within a period of about 5 minutes, 17.2 ml (0.159 mole) phenylisocyanate is added dropwise, care being taken that the temperature during this addition does not exceed 30° C. At the end of the addition, the reaction mixture is stirred for a further 3 hours at room temperature and then is concentrated at 40° C. under an oil pump vacuum.

The residue is reacted with 150 ml ice water; the greasy crystals (1,3-diphenylurea) formed were separated off with suction, washed with 50 ml water and discarded. The water phase is added to a solution of 12.75 ml (0.159 mole) concentrated hydrochloric acid in 50 ml water. The colorless crystals are separated off and dried. The crystallization is carried out using toluene.

Yield: 25.2 g=60.5% of theory.
Fp.: 137°38° C.
DC: flow agent=acetic ester $R_f$-value: 0.570.
Analysis: calculated: C 51.37% H 3.84% N 21.36%. found: C 51.54% H 4.14% N 21.35%.

EXAMPLE II 1-butyryl-3-phenyl-1-(1,2,3-thiadiazole-5-yl)-urea 13.2 g (0.077 mole) butyric acid-N-(1,2,3-thiadiazole-5-yl)-amide were dissolved in 150 ml absolute tetrahydrofuran and reacted with 3.36 g (0.077 mole) of a 55% dispersion of sodium hydride in oil, whereby during the addition the reaction solution through cooling is maintained at 30° C. After about 30 minutes of stirring at room temperature, the evolution of hydrogen is completed. 8.3 ml (0.077 mole) phenylisocyanate is added dropwise within about 5 minutes during which time the reaction temperature increases to 36° C. The reaction mixture is then stirred at room temperature for 1.5 hours whereby a thick crystaline slurry is formed. The reaction mixture is then introduced into a solution of 12.3 ml (0.154 mole) concentrated hydrochloric acid in 300 ml of water. Thereafter the reaction mixture is extracted with 250 ml acetic ester, the organic phase washed with water, dried over magnesium sulfate, filtered and concentrated in vacuum. There were thusly obtained colorless crystals which were digested with 50 ml diisopropylether.

yield: 21.0 g–93.6% of theory.
Fp.: 112°–115° C.
DC: flow agent=acetic ester $R_f$-value: 0.625.
Analysis: calculated: C 53.78% H 4.86% N 19.30%. C 54.22% H 5.05% N 18.92%.

In an analogous manner the following compounds were prepared.

| Name | Physical constant |
|---|---|
| 3-phenyl-1-propionyl-1-(1,2,3 thiadiazole-5-yl)-urea | Fp.: 133° C. |
| 1-isobutyryl-3-phenyl-1-(1,2,3-thiadiazole-5-yl)-urea | Fp.: 157–158° C. |
| 3-phenyl-1-octanoyl-1-(1,2,3-thiadiazole-5-yl)-urea | $n_D^{20}$: 1.5518 |
| 3-phenyl-1-phenylacetyl-1-(1,2,3-thiadiazole-5-yl)-urea | Fp.: 164° C. (decomposition) |

The following examples illustrate the plant growth regulating effect of the compounds of the invention as well as their possibility of use.

EXAMPLE III

In a greenhouse test, the compounds of the invention as set out in the following table were applied in a quantity of 5 kg of active agent per ha at a rate of 60 liters of water spray per ha to the following plants: Sinapis (Si), Solanum (So), Beta (Be), Gossypiom (Go), Hordeum (Ho), Zea mays (Ze), Lolium (Lo) and Setaria (Se) both before and after emergence as indicated. The effect of the treatment was evaluated three weeks thereafter according to the following evaluation scheme:

0=no activity
1–2=growth regulating effect in the form of intense coloration of the primary leaves,
retardation,
growth depression and development of small leaves, reduced root development
3–4=the effect listed under 1–2 but more strongly noticed.

| | Si | | So | | Be | | Go | | Ho | | Ze | | Lo | | Se | |
|---|---|---|---|---|---|---|---|---|---|---|---|---|---|---|---|---|
| Compound of the invention | V | N | V | N | V | N | V | N | V | N | V | N | V | N | V | N |
| 3-phenyl-1-propionyl-1-(1,2,3-thiadiazole-5-yl)-urea | 3 | 4 | 2 | 2 | 3 | 4 | 2 | 4 | 0 | 2 | 2 | 3 | 3 | 3 | 3 | 4 |
| 1-butyryl-3-phenyl-1-(1,2,3-thiadiazole-5-yl)-urea | 3 | 4 | 3 | 3 | 3 | 4 | 2 | 4 | 1 | 2 | 1 | 3 | 1 | 2 | 3 | 4 |
| 1-isobutyryl-3-phenyl-1-(1,2,3-thiadiazole-5-yl)-urea | 3 | 3 | 0 | 0 | 3 | 4 | 0 | 4 | 0 | 0 | 0 | 1 | 0 | 2 | 2 | 4 |
| 3-phenyl-1-octanoyl-1-(1,2,3-thiadiazole-5-yl)-urea | 3 | 4 | 3 | 3 | 3 | 4 | 2 | 4 | 0 | 2 | 1 | 2 | 2 | 3 | 2 | 4 |
| 3-phenyl-1-phenylacetyl-1-(1,2,3-thiadiazole-5-yl)-urea | 0 | 3 | 0 | 2 | 3 | 4 | 3 | 3 | 0 | 1 | 1 | 1 | 2 | 2 | 2 | 4 |
| 1-acetyl-3-phenyl-1-(1,2,3-thiadiazole-5-yl)-urea | 0 | 3 | 2 | 2 | 3 | 3 | 3 | 3 | 2 | 3 | 3 | 3 | 3 | 4 | 3 | 3 |

V = before emergence
N = after emergence

EXAMPLE IV

In a greenhouse test, the plants hereinafter noted were before emergence treated with the indicated compounds of the invention in a quantity of 3 kg active agent/ha. The agents were formulated as spray in water and applied at a rate of 500 liter/ha onto the ground. Three weeks after the treatment, the treatment effects were evaluated according to the following scheme based on a 0–10 rating wherein 0–3 is strong, 4–7 is average and 8–10 designates no inhibition whatsoever. Depending on the type of plants and agents the inhibiting effects varied in degree and applicability.

| kg active agent/ha | 3-phenyl-1-propionyl-1-(1,2,3-thiadiazole-5-yl)-urea 3.0 kg | 1-butyryl-3-phenyl-1-(1,2,3-thiadiazole-5-yl)-urea 1.0 kg |
| --- | --- | --- |
| Brassica | 1 | 2 |
| Solanum | 4 | 6 |
| Allium | 3 | 4 |
| Cucumis | 1 | 3 |
| Medicago | 2 | 4 |
| Phaseoulus | 4 | 6 |
| Helianthus | 1 | 2 |
| Stellaria media | 1 | 2 |
| Abutilon theophrasti | 3 | 2 |
| Matricaria Chamomilla | 1 | 0 |
| Viola tricolor | 1 | 1 |
| Centaurea cyanus | 4 | 1 |
| Amaranthus retroflexus | 1 | 2 |
| Galium asparine | 5 | 10 |
| Chrysanthemum segetum | 0 | 0 |
| Ipomea purpurea | 3 | 5 |
| Fagopyrum es. | 8 | 7 |
| Avena fatua | 8 | 8 |
| Alopecurus myosuroides | 6 | 7 |
| Echinochloa crus galli | 4 | 4 |
| Setaria italica | 5 | 5 |
| Digitaria sanguinalis | 3 | 3 |
| Cyperus esculentus | 6 | 4 |
| Sorghum halepense | 2 | 6 |
| Poa annua | 3 | 4 |

| kg active agent/ha | 3-phenyl-1-octanoyl-1-(1,2,3-thiadiazole-5-yl)-urea 1.0 kg |
| --- | --- |
| Brassica | 4 |
| Solanum | 7 |
| Allium | 7 |
| Cucumis | 6 |
| Medicago | 6 |
| Phaseoulus | 6 |
| Helianthus | 7 |
| Stellaria media | 4 |
| Abutilon theophrasti | 9 |
| Matricaria chamomilla | 1 |
| Viola tricolor | 2 |
| Centaurea cyanus | 9 |
| Amaranthus retroflexus | 6 |
| Galium aparine | 10 |
| Chrysanthemum segetum | 2 |
| Ipomea purpurea | 8 |
| Fagopyrum es. | 10 |
| Avena fatua | 9 |
| Alopecurus myosuroides | 9 |
| Echinochloa crus galli | 8 |
| Sataria italica | 9 |
| Digitaria sanguinalis | 5 |
| Cyperus esculentus | 8 |
| Sorghum halepense | 6 |
| Poa annua | 5 |

EXAMPLE V

In a greenhouse test, the plants hereinafter set out were after emergence treated with the compounds of the invention as designated below in amounts of 1 or 3 kg/ha.

The agents were for the treatment applied at a rate of 500 liters of water/ha directly onto the plants. Fourteen days after the treatment, an evaluation was carried out based on the following scheme:

| kg active agent/ha | 3-phenyl-1-phenylacetyl-1-(1,2,3-thiadiazole-5-yl)-urea 1.0 kg | 1-acetyl-3-phenyl-1-(1,2,3-thiadiazole-5-yl)-urea 1.0 kg | 1-isobutyryl-3-phenyl-1-(1,2,3-thiadiazole-5-yl)-urea 3.0 kg |
| --- | --- | --- | --- |
| Brassica | 4 | 1 | 7 |
| Solanum | 7 | 3 | 9 |
| Allium | 7 | 3 | 8 |
| Cucumis | 7 | 1 | 6 |
| Medicago | 9 | 2 | 7 |
| Phaseoulus | 9 | 3 | 8 |
| Helianthus | 8 | 0 | 10 |
| Stellaria media | 3 | 0 | 4 |
| Abutilon theophrasti | 3 | 2 | 8 |
| Matricaria chamomilla | 1 | 1 | 0 |
| Viola tricolor | 1 | 1 | 1 |
| Centaurea cyanus | 7 | 0 | 4 |
| Amaranthus retroflexus | 3 | 0 | 7 |
| Galium asparine | 10 | 2 | 0 |
| Chrysanthemum segetum | 3 | 0 | 1 |
| Ipomea purpurea | 8 | 4 | 9 |
| Fagopyrum es. | 8 | 4 | 2 |
| Avena fatua | 10 | 7 | 10 |
| Alopecurus myosuroides | 9 | 3 | 8 |
| Echinochloa crs galli crus | 7 | 2 | 8 |
| Staria italica Setaria | 7 | 3 | 10 |
| Digitaria sanguinalis | 6 | 3 | 5 |
| Cyperus esculentus | 7 | 3 | 9 |
| Sorghum halepense | 6 | 2 | 10 |
| Poa annua | 6 | 1 | 7 |

0-3 strong growth inhibition
4-7 average growth inhibition
8-10 no growth inhibition The results demonstrate that the compounds of the invention to a great extent inhibit the growth of the plants set out in the table while the growth of the important agricultural crops of peanuts and potato are not inhibited at all.

| kg active agent/ha | 3-phenyl-1-propionyl-1-(1,2,3-thiadiazole-5-yl)-urea 3.0 kg | 1-butyryl-3-phenyl-1-(1,2,3-thiadiazole-5-yl)-urea 3.0 kg |
|---|---|---|
| Solanum | 3 | 2 |
| Allium | 7 | 10 |
| Cucumis | 0 | 0 |
| Medicago | 3 | 2 |
| Phaseolus | 2 | 2 |
| Glycine | 0 | 2 |
| Helianthus | 3 | 3 |
| Stellaria media | 4 | 3 |
| Matricaria chamomilla | 1 | 1 |
| Viola tricolor | 4 | 2 |
| Centaurea cyanus | 1 | 3 |
| Amaranthus retroflexus | 0 | 0 |
| Galium aparine | 10 | 7 |
| Chrysanthemum segetum | 2 | 2 |
| Ipomea purpurea | 5 | 5 |
| Fagopyrum es. | 4 | 2 |
| Avena fatua | 5 | 8 |
| Alopecurus myosuroides | 8 | 6 |
| Echinochloa crus galli | 4 | 8 |
| Setaria italica | 2 | 2 |
| Digitaria sanguinalis | 3 | 3 |
| Cyperus esculentus | 3 | 5 |
| Sorghum halepense | 6 | 5 |
| Poa annua | 4 | 4 |
| Cynodon dactylon | 4 | 8 |
| Agropyron | 5 | 8 |
| peanut | 10 | 10 |
| potato | 10 | 10 |

| kg active agent/ha | 1-isobutyryl-3-phenyl-1-(1,2,3-thiadiazole-5-yl)-urea 1.0 kg | 3-phenyl-1-octanoyl-1-(1,2,3-thiadiazole-5-yl)-urea 1.0 kg |
|---|---|---|
| Solanum | 7 | 5 |
| Allium | 10 | 8 |
| Cucumis | 4 | 0 |
| Medicago | 8 | 9 |
| Phaseolus | 4 | 5 |
| Glycine | 7 | 6 |
| Helianthus | 9 | 5 |
| Stellaria media | 9 | 4 |
| Matricaria chamomilla | 6 | 4 |
| Viola tricolor | 4 | 2 |
| Centaurea cyanus | 8 | 6 |
| Amaranthus retroflexus | 5 | 1 |
| Galium aparine | 10 | 9 |
| Chrysanthemum segetum | 4 | 6 |
| Ipomea purpurea | 7 | 8 |
| Fagopyrum es. | 4 | 3 |
| Avena fatua | 10 | 9 |
| Alopecurus myosuroides | 8 | 9 |
| Echinochloa crus galli | 10 | 10 |
| Sataria italica | 9 | 6 |
| Digitaria sanguinalis | 9 | 8 |
| Cyperus esculentus | 6 | 5 |
| Sorghum halepense | 8 | 9 |
| Poa annua | 9 | 8 |
| Cynodon dactylon | 8 | 9 |
| Agropyron repens | 8 | 8 |
| Peanut | 10 | 10 |
| Potato | 10 | 10 |

| kg active agent/ha | 3-phenyl-1-phenylacetyl-1-(1,2,3-thiadiazole-5-yl)-urea 3.0 kg | 1-acetyl-3-phenyl-1-(1,2,3-thiadiazole-5-yl)-urea 1.0 kg |
|---|---|---|
| Solanum | 4 | 4 |
| Allium | 9 | 10 |
| Cucumis | 0 | 0 |
| Medicago | 6 | 5 |
| Phaseolus | 2 | 5 |
| Glycine | 2 | 3 |
| Helianthus | 7 | 3 |
| Stellaria media | 2 | 3 |
| Matricaria chamomilla | 2 | 2 |
| Viola tricolor | 3 | 3 |
| Centaurea cyanus | 3 | 2 |
| Amaranthus retroflexus | 0 | 0 |
| Galium aparine | 9 | 8 |
| Chrysanthemum segetum | 3 | 2 |
| Ipomea purpurea | 3 | 7 |
| Fagopyrum es. | 2 | 2 |
| Avena fatua | 9 | 6 |
| Alopecurus myosuroides | 9 | 7 |
| Echinochloa crus galli | 5 | 4 |
| Setaria italica | 4 | 4 |
| Digitaria sanguinalis | 7 | 4 |
| Cyperus esculentus | 3 | 4 |
| Sorghum halepense | 8 | 3 |
| Poa annua | 7 | 4 |
| Cynodon dactylon | 7 | 4 |
| Agropyron repens | 4 | 4 |
| Peanut | 10 | 10 |
| Potato | 10 | 10 |

EXAMPLE VI

Cotton plants at a stage where 4-6 leaves have emerged were treated with the following compound of the invention and with the comparison compound as noted. The substances were applied as dispersions in a quantity of 500 liters of water/ha (repeated four times). Twenty days later the percent of dropped leaves was determined. The result can be seen from the following table.

| Compound of the Invention | Doses in g active agent | defoliation in % |
|---|---|---|
| 1-acetyl-3-phenyl-1-(1,2,3-thiadiazole-5-yl)-urea | 500 | 100 |
| Comparison Compound | | |
| 1-phenyl-3-(1,2,3-thiadiazole | 500 | 42.9 |

-continued

| Compound of the Invention | Doses in g active agent | defoliation in % |
|---|---|---|
| 5-yl)-urea | | |

EXAMPLE VII

Cotton plants at a stage where 5-6 leaves have emerged were treated as set out in Example IV and then evaluated for effectiveness of the compounds used as a plant growth regulators. The results of this example can be seen from the table which follows:

| Compound of the Invention | Doses in g active agent/ ha | Defoliation in % |
|---|---|---|
| 3-phenyl-1-propionyl-1-(1,2,3-thiadiazole-5-yl)-urea | 500 | 100 |
| 1-butyryl-3-phenyl-1-(1,2,3-thiadiazole-5-yl)-urea | 500 | 85.7 |
| 1-octanoyl-3-phenyl-1-(1,2,3-thiadiazole-5-yl)-urea | 500 | 57.1 |
| 1-phenylacetyl-3-phenyl-1-(1,2,3-thiadiazole-5-yl)-urea | 500 | 52.4 |
| Comparison Compound | | |
| 1-phenyl-3-(1,2,3-thiadiazole-5-yl)-urea | 500 | 40.9 |

What is claimed is:

1. A 1,2,3-thiadiazole-5-yl urea derivative of formula

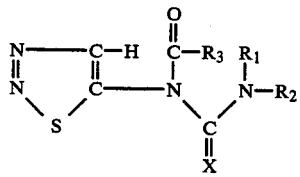

wherein $R_1$ is hydrogen or $C_1$-$C_4$-alkyl; $R_2$ is $C_1$-$C_4$-alkyl, $C_5$-$C_8$-cycloalkyl, phenyl, halogenophenyl, $C_1$-$C_4$-alkylphenyl, $C_1$-$C_4$-alkoxyphenyl, nitrophenyl or tifluoromethyl phenyl; $R_3$ is hydrogen, $C_1$-$C_{10}$-alkyl, fluoromethyl, methoxymethyl, phenoxymethyl, 1-phenoxyethyl, 2-phenoxyethyl (2,4-dichlorophenoxy)-methyl, $C_2$-$C_8$-aklenyl, benzyl, $C_3$-$C_8$-cycloalkyl, phenyl, 2-chlorophenyl, 3-chlorophenyl, 3-methylphenyl, 4-methylphenyl, 3-nitrophenyl, 4-nitrophenyl, 2-methoxyphenyl, 4-methoxyphenyl, 1-naphthyl, or 2-furyl, and X is oxygen or sulfur.

2. A compound according to claim 1 designated 1-acetyl-3-phenyl-1-(1,2,3-thiadiazole-5-yl)-urea.

3. A compound according to claim 1 designated 1-butyryl-3-phenyl-1-(1,2,3-thiadiazole-5-yl)-urea.

4. A compound according to claim 1 designated 3-phenyl-1-propionyl-1-(1,2,3-thiadazole-5-yl)-urea.

5. A compound according to claim 1 designated 1-isobutyryl-3-phenyl-1-(1,2,3-thiadiazole-5-yl)-urea.

6. A compound according to claim 1 designated 3-phenyl-1-octanoyl-1-(1,2,3-thiadiazole-5-yl)-urea.

7. A compound according to claim 1 designated 3-phenyl-1-phenylacetyl-1-(1,2,3-thiadiazole-5-yl)-urea.

8. A plant growth regulating and defoliating composition comprising a 1,2,3-thiadiazole-5-yl-urea derivative according to claim 1 as active agent in admixture with an agricultural carrier.

9. A plant growth regulating and defoliating agent according to claim 8 containing about 5 to 95% of active agent and 95 to 5 weight % of said carrier.

10. A plant growth regulating and defoliating composition according to claim 8 additionally containing at least one member selected from the group consisting of plant protection agents, pest control agents, fertilizers, herbicides, wetting agents, emulsifiers, solvents, oils, and surface active agents.

11. A method for plant growth regulation which comprises applying to the plant and/or its habitat in an amount sufficient to effect such growth regulation a compound according to claim 1.

12. A method for defoliating plants which comprises applying to the plant and/or its habitat in an amount sufficient to effect such defoliation a compound according to claim 1.

13. A method for defoliating plants according to claim 12, wherein said plant is cotton.

14. A method for defoliating plants according to claim 12, wherein said compound is applied in an amount of 0.05 to 5 kg/ha.

* * * * *